(12) United States Patent
O'Hare et al.

(10) Patent No.: US 9,463,082 B2
(45) Date of Patent: Oct. 11, 2016

(54) METHOD OF FORMING A TISSUE SCAFFOLD

(75) Inventors: Peter O'Hare, Northern Ireland (GB);
George Burke, Northern Ireland (GB);
Brian Meenan, Northern Ireland (GB);
Patrick Porter, Northern Ireland (GB);
Chris Rea, Northern Ireland (GB)

(73) Assignee: University of Ulster, Northern Ireland (GB)

(*) Notice: Subject to any disclaimer, the term of this patent is extended or adjusted under 35 U.S.C. 154(b) by 77 days.

(21) Appl. No.: 14/235,321

(22) PCT Filed: Jul. 30, 2012

(86) PCT No.: PCT/IB2012/053888
§ 371 (c)(1),
(2), (4) Date: Mar. 31, 2014

(87) PCT Pub. No.: WO2013/018021
PCT Pub. Date: Feb. 7, 2013

(65) Prior Publication Data
US 2014/0207250 A1    Jul. 24, 2014

(30) Foreign Application Priority Data

Jul. 29, 2011    (GB) .................................. 1113060.6

(51) Int. Cl.
*B29C 70/68* (2006.01)
*B29C 71/02* (2006.01)
(Continued)

(52) U.S. Cl.
CPC . *A61F 2/02* (2013.01); *A61F 2/04* (2013.01);
*A61L 27/34* (2013.01); *A61L 27/56* (2013.01);
(Continued)

(58) Field of Classification Search
CPC .......... A61F 2/04; B23P 17/00; B29C 70/68;
B29C 71/02; B32B 1/08; D01D 5/0007;
D01D 5/0015; D01D 5/0023; D01D 5/003;
D01D 5/0038; D01D 5/0046; D01D 5/0076;
D01D 5/0084; D01D 5/0092; D01D 10/02
USPC ....... 264/10, 171.1, 211.17, 211.2, 234, 255,
264/259, 464, 465, 466, 483, 484; 29/527.1
See application file for complete search history.

(56) References Cited

U.S. PATENT DOCUMENTS

2003/0100944 A1    5/2003  Laksin et al.
2006/0253192 A1    11/2006 Atala et al.
(Continued)

FOREIGN PATENT DOCUMENTS

JP          2008075197 A  *  4/2008  .............. D04H 1/72
WO    WO 2011/113001      9/2011

OTHER PUBLICATIONS

Prabhakaran et al., "*Surface Modified Electrospun Nano fibrous Scaffolds for Nerve Tissue Engineering*", Nanotechnology, vol. 19, No. 45, Nov. 12, 2008.
(Continued)

*Primary Examiner* — Leo B Tentoni
(74) *Attorney, Agent, or Firm* — Diederiks & Whitelaw, PLC (57) ABSTRACT

A process of forming a tissue scaffold is described, the process comprising electrospinning polymer fibers from a spinneret onto a tissue scaffold template. In embodiments, the fibers are plasma-treated between the spinneret and the template. The scaffold may be constructed of alternating layers of aligned and randomly oriented fibers. The scaffold may be heat treated to control the mechanical properties of the scaffold, such as density, pore size and pore interconnectivity.

6 Claims, 5 Drawing Sheets

(51) Int. Cl.
*B32B 1/08* (2006.01)
*D01D 10/02* (2006.01)
*A61F 2/02* (2006.01)
*D01D 5/00* (2006.01)
*A61L 27/34* (2006.01)
*A61L 27/56* (2006.01)
*A61L 31/10* (2006.01)
*A61L 31/14* (2006.01)
*D01D 10/00* (2006.01)
*A61F 2/04* (2013.01)

(52) U.S. Cl.
CPC .............. *A61L 31/10* (2013.01); *A61L 31/146* (2013.01); *D01D 5/003* (2013.01); *D01D 5/0038* (2013.01); *D01D 5/0076* (2013.01); *D01D 5/0084* (2013.01); *D01D 5/0092* (2013.01); *D01D 10/00* (2013.01); *A61L 2420/08* (2013.01); *A61L 2430/20* (2013.01); *A61L 2430/22* (2013.01)

(56) References Cited

U.S. PATENT DOCUMENTS

| | | | |
|---|---|---|---|
| 2007/0152378 A1* | 7/2007 | Kim | .............................. 264/465 |
| 2008/0131965 A1 | 6/2008 | Baaijens | |
| 2010/0168832 A1 | 7/2010 | Neuenschwander | |
| 2010/0222771 A1 | 9/2010 | Mitchell et al. | |
| 2010/0327494 A1 | 12/2010 | Jabbari | |
| 2011/0250689 A1 | 10/2011 | Baaijens et al. | |
| 2011/0260584 A1* | 10/2011 | Yu | ........................ D01D 5/0038 264/484 X |
| 2013/0150947 A1* | 6/2013 | Kaufmann et al. | .......... 623/1.15 |
| 2014/0025156 A1 | 1/2014 | Baaijens | |
| 2014/0079759 A1* | 3/2014 | Patel et al. | .................... 424/443 |

OTHER PUBLICATIONS

Lee et al., "*The Use of Thermal Treatments to Enhance the Mechanical Properties of Electrospun Poly(ε-caprolactone) Scaffolds*", Biomaterials, vol. 29, No. 10, Dec. 21, 2007, pp. 1422-1430.

Vaz et al., "*Design of Scaffolds for Blood Vessel Tissue Engineering Using a Multi-Layering Electrospinning Technique*", Acta Biomaterialia, vol. 1, No. 5, Sep. 1, 2005, pp. 575-582.

Del Gaudio et al., "*Electrospun Bioresorbable Trileaflet Heart Valve Prosthesis for Tissue Engineering: in vitro Functional Assessment of a Pulmonary Cardiac Valve Design*", vol. 44, No. 2, Jan. 1, 2008, pp. 178-186.

Koens, "*Park I: From a Parameterized Computer Model of the Aortic Valve to a Stentless 3D Scaffold and Functional Evaluation*", Nov. 19, 2004, pp. 1-14.

* cited by examiner

CSLM Human Dermal Fibroblast Cells on PCL + Rhodamine

Figure 4

SEM - Human Dermal Fibroblast Cells on PCL

Figure 5

CSLM Human Mesenchymal Stem Cells on PCL + Rhodamine

Figure 6

SEM - Human Mesenchymal Stem Cells on PCL

Figure 7

SEM - Human Dermal Keratinocyte Cells on PCL

Figure 8

SEM - Human Umbilical Vein Endothelial Cells on PCL

METHOD OF FORMING A TISSUE SCAFFOLD

CROSS-REFERENCE TO RELATED APPLICATIONS

This application represents a National Stage application of PCT/IB2012/053888 entitled "Tissue Scaffold" filed Jul. 30, 2012, pending.

BACKGROUND OF THE INVENTION

The present invention relates to methods of forming a tissue scaffold.

The present invention is applicable to the formation of tissue scaffolds for any suitable use. For example, the tissue scaffolds formed may be used in forming replacement heart valves, vascular grafts, myocardial patches, respiratory and tracheal grafts, skin grafts or indeed any type of tissue graft. Similarly the invention could be used to engineer and produce scaffolds for the synthesis of any organ, partial or complete. Tissue scaffolds formed in accordance with any aspect of the present invention can be used for any tissue engineering/augmentation application such as vascular grafts, intestinal grafts, tracheal grafts, oesophageal grafts, etc, and may be combined with a stent, as described below, in certain applications.

The present invention in some preferred embodiments relates to the formation of a tissue scaffold for forming replacement heart valves. The current treatments for Heart Valve Replacement (HVR) are mechanical valves (metal or polymer) or bio-prosthetic valves from animal/deceased donor heart. In the latter type, cells and cellular debris are removed from the valve, leaving only the "scaffold" of the valve tissue. However, notwithstanding the surgical risks, there are still many problems associated with these types of HVRs. In the case of mechanical valves, they have the potential to undergo actual mechanical failure as they have a limited lifespan (8-10 years) and are prone to calcification/clotting. Furthermore, they produce an audible clicking sound in use which some patients are very conscious of. Although bio-prosthetic valves are made from a de-cellularised biological source, thus addressing some of the issues associated with mechanical valves, there is still a large risk of disease transfer and, more importantly, immuno-rejection of the implant by the patient. Both of these implant types are permanent implants as they are not resorbed by the body. As a result, new heart tissue formation and regeneration, if any, is therefore limited.

Although attempts have been made to engineer HVRs by electrospinning fibers to form artificial scaffolds, they have failed to generate scaffolds which adequately mimic the biological and mechanical properties of natural donor scaffolds from bio-prosthetic valves.

While some of the benefits of the present invention have been illustrated by reference to the context of engineering HVRs, it will be appreciated that the invention is not limited to this application, and provides similar benefits in the formation of tissue scaffolds for other purposes. For example, the methods of the present invention may produce tissue scaffolds for other applications, such as grafts or any other application as discussed above, which more closely mimic the biological and mechanical properties of natural e.g. donor scaffold structures.

The present invention attempts to overcome or mitigate the disadvantages of known techniques by providing novel methods for forming a tissue scaffold.

SUMMARY OF THE INVENTION

Accordingly, from a first aspect, the present invention provides a method of forming a tissue scaffold, the method comprising: providing an electrospinning apparatus comprising a spinneret and a tissue scaffold template spaced from the spinneret; electrospinning a polymer from the spinneret onto the template to form the tissue scaffold; and exposing the polymer to a plasma.

The electrospinning process generates nano- or microscale polymer fibers which are deposited on a scaffold template to form a tissue scaffold having the desired shape. Exposing the polymer fibers to either a hot or cold plasma alters the surface chemistry, surface charge and surface energy of the fibers to increase wettability of the fibers (or surface chemistry), thus increasing cell adhesion, attachment, migration and proliferation of the scaffold, both in vitro and in vivo. The plasma-treated polymer scaffold therefore more closely mimics the biological properties of a natural donor scaffold. Advantageously, the present invention eliminates the need to "pre-seed" the polymer scaffold with cells prior to implantation, as is required with prior art polymer scaffolds. Furthermore, plasma treatment is a convenient and low-cost technique of modifying the surface properties of the polymer fibers without affecting the bulk mechanical properties of the scaffold.

In some embodiments, the plasma treatment step can take place between the spinneret and the template, i.e. the polymer fibers are plasma-treated as they are formed during the electrospinning process, and prior to being deposited on the scaffold template. This eliminates the need for a separate plasma treatment step after the scaffold has been formed. The plasma treatment can take place anywhere between the spinneret and the template. In other embodiments, the plasma treatment can be applied to the tissue scaffold as a final stage after the deposition process has been completed and not during the deposition process itself.

In embodiments in which the plasma treatment step takes place between the spinneret and the template, the apparatus may further comprise an anode and a cathode spaced apart from the anode, the anode and the cathode being positioned between the spinneret and the template. This can be in any arrangement or conformation that does not inhibit the deposition of the polymer onto the template. By applying a sufficient voltage to each of the anode and the cathode, a region of plasma can be generated in the gap therebetween. The polymer is then electrospun through the region of plasma and onto the template. A range of different voltages can be used, depending on the particular application. The voltage may be constant, or the voltage (and therefore the plasma) can be applied intermittently or 'pulsed' in order to help control the effects of the plasma on the polymer material. Plasma treatment may, in preferred embodiments, be carried out using atmospheric gases. However, it is envisaged that processing gases may be used, such as nitrogen or ammonia. The treatment may, for example, be carried out under ambient conditions.

In some embodiments, the method may further comprise the steps of: electrospinning a first polymer layer onto the template; and electrospinning a second polymer layer onto the template; wherein the template rotates during the electrospinning of one of the first and second layers, and wherein the template does not rotate during the electrospinning of the other of the first and second layers. Such a method produces a layer of aligned fibers and a layer of randomly oriented fibers. Specifically, rotation of the template during the deposition process generates a layer of aligned fibers, whereas a stationary template results in a layer of randomly oriented fibers. Each layer (random or aligned) could be of the same or differing fibre densities or thicknesses, controlled by the deposition time, in order to produce the desired material/mechanical/biological function.

By producing a tissue scaffold having a layer of aligned fibers and a layer of randomly oriented fibers, it is possible to generate a scaffold having mechanical properties which more closely match those of a natural donor scaffold, e.g. stiffness and strength. The degradation rate and the desired biological interactions of an implanted scaffold can also be controlled using this method.

This is itself a novel and inventive method, so from a second aspect the present invention provides a method of forming a tissue scaffold, the method comprising: electrospinning a first polymer layer onto a tissue scaffold template; and electrospinning a second polymer layer onto the template; wherein the template rotates during the electrospinning of one of the first and second layers, and wherein the template does not rotate during the electrospinning of the other of the first and second layers.

In embodiments combining the plasma treatment step with the formation of a layered tissue scaffold, the plasma treatment can be applied only to selected layers, or to all of the layers.

In accordance with the invention in any of its aspects or embodiments which include forming a layered tissue scaffold, the polymer used to form each of the first and second layers may be the same or may be different. Additional alternating layers of aligned fibers and randomly oriented fibers can be added to control the mechanical and biological properties of the tissue scaffold, as required.

In embodiments of both the first and the second aspects of the invention, the method may further comprise a step of heat treating the electrospun tissue scaffold at a temperature of between 20° C. and 200° C. to alter at least one of the density of the scaffold, the pore size of the scaffold and the pore interconnectivity, or combinations thereof. For example, the heat treatment step can be used to make the tissue scaffold contract onto the template, thus producing a more accurate shape. Furthermore, the heat treatment step can be used to alter the pore size and the pore interconnectivity such that the biological properties of the scaffold more closely match those of a natural donor scaffold. It will be appreciated that the heat treatment heats the scaffold above ambient temperature, and thus the temperature used in heat treatment should be selected so as to provide a heating effect relative to the ambient temperature.

This is itself a novel and inventive method, so from a third aspect the present invention provides a method of forming a tissue scaffold, the method comprising: electrospinning a polymer onto a tissue scaffold template to form a tissue scaffold; and heat treating the electrospun tissue scaffold at a temperature of between 20° C. and 200° C. to alter at least one of the density of the scaffold, the pore size of the scaffold and the pore interconnectivity or any combination thereof. Preferably, the heat treatment is carried out before the scaffold is removed from the template.

In embodiments of the invention according to any of its aspects, the polymer used to form the scaffold may comprise at least one of polylactic acid, polylactic-co-glycolic acid, polycaprolactone, and mixtures thereof. The polymer may be a biopolymer having the appropriate biological properties for the particular application. Any suitable polymer that exhibits appropriate biocompatibility properties may be used. Numerous such polymers are known in the art. For example, a polymer approved for medical use by a regulator may suitably be used.

In some embodiments, the tissue scaffold formed by the present invention is a heart valve scaffold. However, the skilled person will realise that the present invention applies equally to the formation of tissue scaffolds for other uses, such as vascular grafts, myocardial patches, respiratory and tracheal grafts, skin grafts or indeed any type of tissue graft. Similarly the invention could be used to engineer and produce scaffolds for the synthesis of any organ, partial or complete. Tissue scaffolds formed in accordance with any aspect of the present invention can be used for any tissue engineering/augmentation application such as vascular grafts, intestinal grafts, tracheal grafts, oesophageal grafts, etc, particularly when combined with a stent, as described below. The present invention extends to such uses. As the examples below illustrate, the present invention may be used to obtain tissue scaffolds which are subsequently to be populated by a wide range of cells, for example ranging from coronary artery cells to dermal cells, or stem cells. The present invention extends to an electrospun tissue scaffold obtained in accordance with the methods of the invention in any of their aspects or embodiments. The method further extends to the step of culturing cells on an electrospun tissue scaffold obtained in accordance with the invention of any of its aspects or embodiments, and to an electrospun tissue scaffold obtained in accordance with the invention in any of its aspects or embodiments having cells attached thereon. The cells may be of any type e.g. of any of the types exemplified herein.

In some embodiments of the invention according to any of its aspects, the method may further comprise a step of incorporating a stent into the tissue scaffold. The stent could be mounted onto the template before the deposition process begins permitting the stent to be incorporated into the scaffold structure during the polymer fibre deposition process. The stent could also be attached by physical, chemical, mechanical or any other means, inside or outside the scaffold structure in order to aid this function or to aid a mechanical or additional structural function after the scaffold has been made or at any stage during the deposition process. The stent could be applied to the scaffold after the deposition process has been completed. In embodiments where the tissue scaffold is a heart valve scaffold, the stent can aid in the deployment of the heart valve scaffold via a minimally invasive transcather surgical procedure.

BRIEF DESCRIPTION OF THE DRAWINGS

In some embodiments, the stent is a metal stent. The metal can be stainless steel, titanium, cobalt chromium alloy, platinum chromium alloy, nitinol, combinations thereof, or any other commonly or uncommonly used metal stent material. Embodiments of the invention will now be described by way of example only and with reference to the drawings in which.

DETAILED DESCRIPTION OF THE INVENTION

Figure 1:
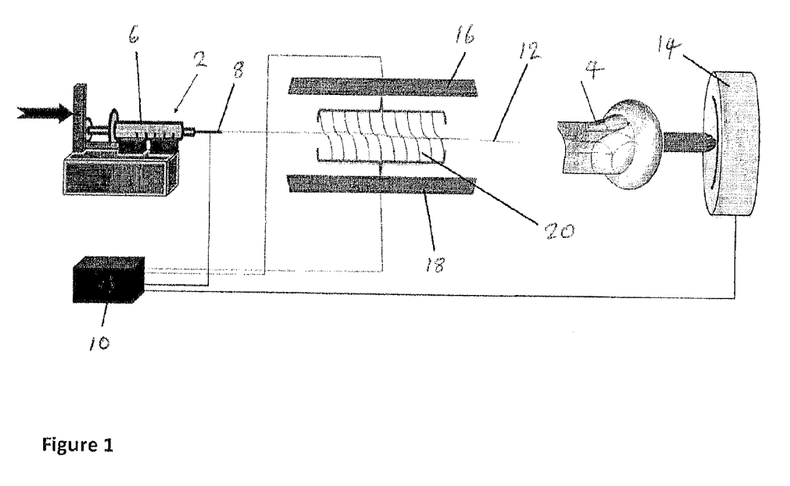
FIG. 1 shows an exemplary electrospinning arrangement in accordance with the present invention.
Figure 2:
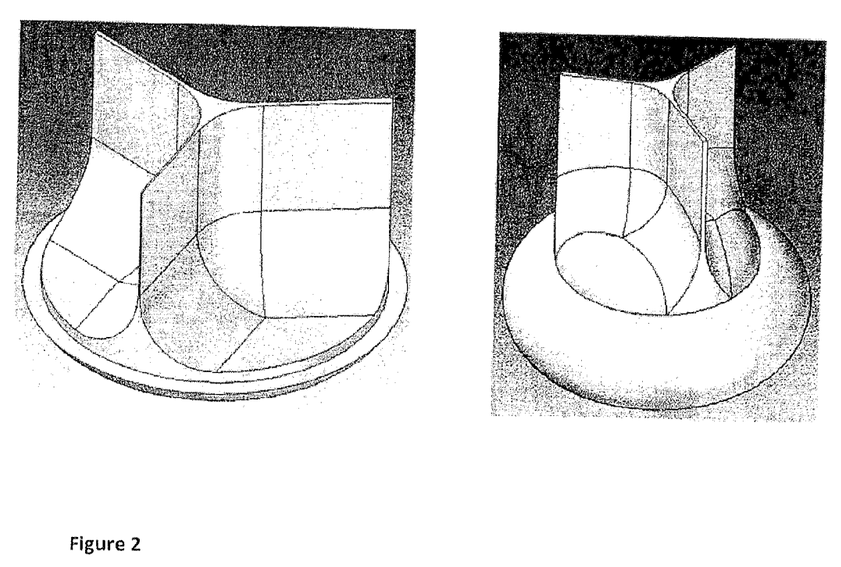
FIG. 2 shows exemplary heart valve templates for forming heart valve tissue scaffolds.

FIG. 1 shows an electrospinning apparatus comprising a spinneret 2 and a scaffold template 4. In the embodiment shown in FIG. 1, the template is a tricuspid heart valve template, although any other form of valve or other tissue scaffold templates can be used depending on the shape required. Exemplary tricuspid heart valve templates are shown in more detail in FIG. 2.

The spinneret 2 comprises a syringe 6 containing a liquid polymer solution, and a needle 8 through which the polymer solution is discharged during the electrospinning process. A power supply 10 provides an electrical bias to the needle 8 so as to charge the polymer solution as it is discharged through the needle 8. In a known manner, the electrostatic forces within the charged polymer solution overcome the surface tension of the liquid, causing the solution to splay into a stream of fibers 12. The fibers, in nanofiber or microfiber dimension, are deposited onto a grounded or oppositely biased collector. In the illustrated embodiment, the scaffold template 4 also functions as the collector.

The polymer may be chosen as desired as known in the art for producing a tissue scaffold for a given application. Such polymers exhibit suitable biocompatibility properties. In practice, polymers which have been approved for medical use by regulators may be appropriate for use in obtaining the tissue scaffold. It has been found that electrospinning processes do not have a significant impact upon the bulk properties of the polymer. It is believed that the additional plasma treatment step carried out in accordance with the invention will not detract from, and may enhance the biocompatibility properties of polymers.

The polymer used may be synthetic or may be a biopolymer, or may include combinations thereof. For example, the polymer may be or comprise at least one of polylactic acid, polylactic-co-glycolic acid, polycaprolactone, and mixtures thereof. The invention will be illustrated below in relation to some examples in which the polymer is or comprises polycaprolactone (PCL). However, it will be appreciated that this is merely a preferred example of a polymer which may be used.

The apparatus may further comprise a motor 14 for rotating the template 4 during the deposition process. Rotating the template 4 aligns the deposited fibers, thus providing a more uniform layer. In embodiments on the invention, the tissue scaffold is built up in layers, wherein the template 4 is rotated during the deposition of some layers and not others, so as to provide some layers comprising aligned fibers and some layers comprising randomly oriented fibers. To provide optimum control over the mechanical and biological properties of the scaffold, the layered scaffold is preferably constructed using alternating layers of aligned and randomly oriented fibers. The layers may be of the same or different thicknesses and densities.

As known in the art, the electrospinning apparatus is housed in a suitable sealed chamber, which is in communication with an extractor fan to provide an appropriate extraction fan flow rate during the process for e.g. removing fumes emanating from a solvent of the polymer. The extraction fan flow rate may be selected appropriately taking into account the desired scaffold morphology as known in the art. The housing enables control over temperature, humidity and extraction to be maintained during the electrospinning process.

In the illustrated embodiment, the apparatus also includes an anode 16 and a cathode 18 which are spaced apart either side of the fiber stream 12. This anode and cathode arrangement can be configured in many different forms anywhere in the area between the motor 14 and the syringe 6, or anywhere between the template 4 and the syringe 6. The anode 16 and the cathode 18 are biased by the power supply 10 so as to form a potential difference therebetween. Alternatively, the anode and the cathode may be biased using a different power supply.

At a sufficiently high voltage, the gas between the anode and the cathode becomes ionised, thus forming a region of plasma 20 through which the fiber stream 12 passes. The plasma power and number of cycles can be selected appropriately for each scaffold, and the skilled person will understand how to optimise these parameters for a given scaffold. Typical operating powers may be between 500-1000 W. The plasma alters the surface charge of the polymer fibers, thus improving their wettability and increasing cell adhesion, attachment, migration and proliferation in the finished scaffold. As such, a scaffold formed from plasma-treated polymer fibers in accordance with the invention does not required "pre-seeding" with cells before implantation into the patient. Plasma treatment may be carried out using atmospheric gases under ambient conditions, although it is envisaged that other processing gases e.g. nitrogen or ammonia could be used.

In some embodiments, the scaffold obtained in accordance with the invention in any of its embodiments may be subjected to a heat treatment after deposition of the fibers onto the template 4. For example, the scaffold may be heated to a temperature of between 20° C. and 200° C. The heat treatment can aid contraction of the scaffold onto the template 4, thus ensuring that the scaffold assumes the correct shape, as required. The heat treatment can also be used to control the mechanical and biological properties of the scaffold so as to more closely match those of a natural donor scaffold. For example, the heat treatment can be used to alter the density of the scaffold, as well as the pore size and pore interconnectivity.

It will be understood that the above is a description of some preferred embodiments and that many variations are possible within the scope of the invention, as determined by the claims. In particular, the methods of the present invention are not limited to the production of tissue scaffolds in the form of heart valve scaffolds. The following examples are provided for illustrative purposes alone and should similarly not be considered to limit the scope of the invention, as set forth in the claims.

EXAMPLES

Heart Valve Scaffold Formation

In one example, it was been found that the following conditions were particularly suitable for the formation of a tissue scaffold that is in the form of a heart valve scaffold of a given dimension i.e. thickness.

The polymer used was a PCL (polycaprolactone) polymer obtained from PURAC®. The polymer was PURASORB® PLC 7015 70/30 L-lactide/caprolactone copolymer, IV midpoint 1.5 dl/g. The composition was as follows;
Comonomer ratio, L-lactide 68 mol %
Comonomer ration, Caprolactone 32 mol %
water content max 0.5%
Tin content max 100 ppm
Residual solvent max 0.1%
Residual monomer max 0.5%
It is understood that the quantity of heavy metals present would comply with USP test methods for the presence of heavy metals if tested.

The PCL polymer was present at 10% weight by volume in a solvent comprising 90% chloroform and 10% dimethylformamide (DMF). A voltage of 10 kV was applied to the spinneret, and the polymer flow rate was 1 ml/hour. The ambient temperature within the apparatus housing was approximately 23 degrees Celsius. The needle gauge was 18 G. An extractor fan coupled to the housing was set at a high level to rapidly remove the evaporating fumes from the solvents.

Cell Scaffold Interaction

By way of background, the examples described below by reference to FIGS. 3 to 9 relate to some testing carried out to illustrate the properties of electrospun tissue scaffolds and the interaction of various cells therewith. It is demonstrated that an electrospun polymer tissue scaffold is suitable for the culture of various types of cell, which may be used for a variety of tissue engineering applications. In these tests the relevant cell type was cultured on a representative model electrospun polymer surface. The interaction of the surface with the following cell types was studied;
Human Primary Mesenchymal Stem Cells (MSCs)
Human Primary Coronary Artery Smooth Muscle Cells (HCASMs)
Human Primary Umbilical Vein Endothelial Cells (HUVECs)
Human Primary Dermal Fibroblasts (HDFs)
Human Dermal Keratinocyte Cell Line (HaCats)

Figure 3:
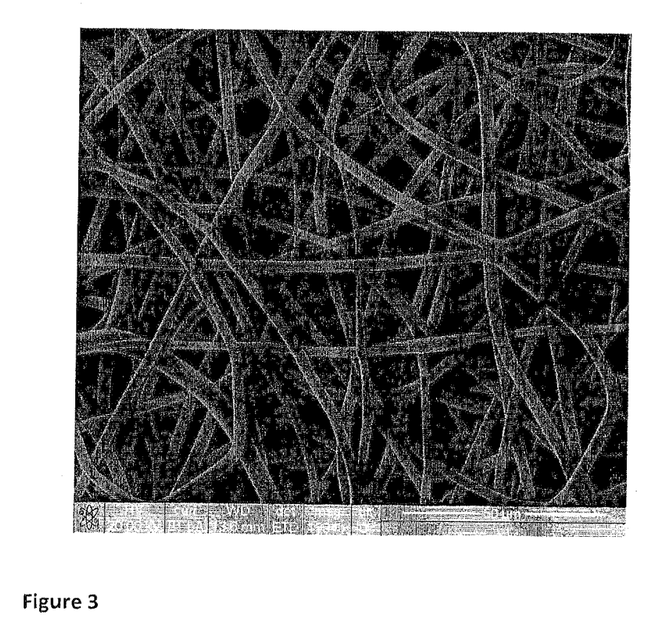
FIG. 3 is an image of an electrospun polycaprolactone (PCL) scaffold.

FIG. 3 is a scanning electron micrograph illustrating the structure of fibers in a part of a test electrospun scaffold obtained by electrospinning the polymer polycaprolactone (PCL). As discussed above, this is an exemplary polymer which may be used in accordance with the invention. To improve contrast, the polymer included 50 μg/ml Rhodamine B. In this exemplary scaffold, the average fiber diameter was found to be 3.33 μm+/−0.7 μm.

The electrospinning was carried out using an apparatus similar to that of FIG. 1, but plasma treatment was not implemented in obtaining the test scaffold for these background examples. The template was not rotated during the electrospinning process. The electrospinning conditions were as exemplified above under the section entitled "Heart Valve Scaffold Formation". Thus the composition used was using 10% weight by volume of the PCL polymer PURASORB® PLC 7015 70/30 L-lactide/caprolactone copolymer, IV midpoint 1.5 dl/g, in a solvent comprising 90% chloroform and 10% dimethylformamide (DMF). A voltage of 10 kV was applied to the spinneret, and the polymer flow rate was 1 ml/hour. The ambient temperature within the apparatus housing was approximately 23 degrees Celsius. The needle gauge was 18 G. An extractor fan coupled to the housing was set a high level to rapidly remove the evaporating fumes from the solvents. The scaffold obtained was not subjected to heat treatment prior to being populated with cells.

FIGS. 4 to 9 illustrate the results of some testing in which various cells were caused to grow on a PCL electrospun scaffold formed obtained and illustrated in FIG. 3. These Figures illustrate the suitability of the electrospun PCL fibers as a tissue scaffold for different types of cells.

Figure 4:
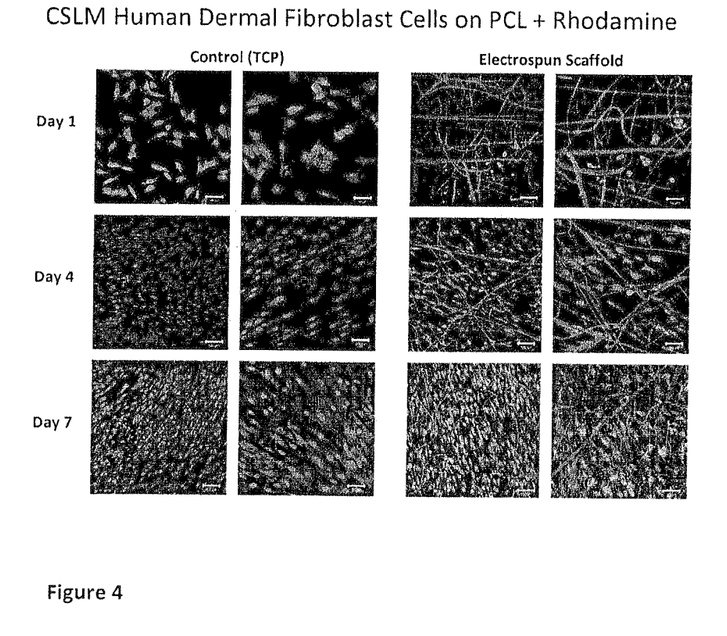
FIGS. 4 and 5 illustrate growth of human primary dermal fibroblast (hDF) cells on an electrospun PCL scaffold.

FIG. 4 shows the results of a comparative test in which Human Primary Dermal Fibroblast Cells were cultured on the electrospun PCL scaffold, and on a control tissue culture plastic (TCP) surface. This was achieved using a suitable growth medium for cell culture as known in the art. The growth medium selected for any of the cells exemplified herein may be in accordance with guidance from the supplier of the cells in question or relevant published literatures as known in the art. In this case, a "Normal growth medium" was used, being a DMEM (high glucose) supplemented with 10% fetal bovine serum and 1% penicillin/streptomycin.

As discussed above, the dye Rhodamine B was used to improve visibility of the electrospun PCL scaffold. The photomicrographs of FIG. 4 were taken using a Confocal Laser Scanning Microscopy (CSLM) technique. For each of the control and electrospun scaffold, the images shown include images of two levels of resolution taken on day 1 of the test, and also on day 4 and day 7. The day of the test refers to the day relative to the start of the test, when the scaffold(s) were initially populated with cells i.e. the start of cell culture. Day 1 refers to 24 hours from the start of the test, day 4 being 96 hours etc.

Figure 5:
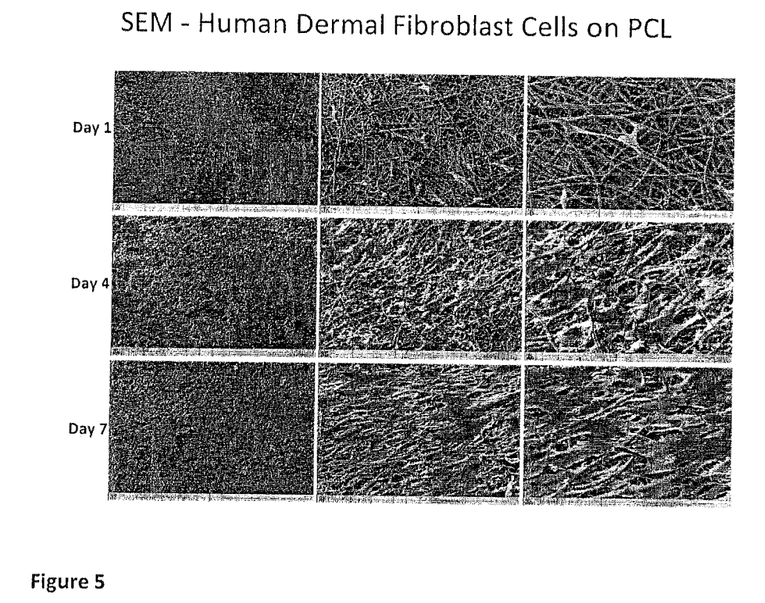

FIG. 5 includes images of the Human Primary Dermal Fibroblast Cells on the PCL scaffold on days 1, 4 and 7, taken instead using a Scanning Electron Microscopy (SEM) technique, and with three levels of increasing magnification for each day. This illustrates the cell growth which took place on the electrospun polymer scaffold.

Figure 6:
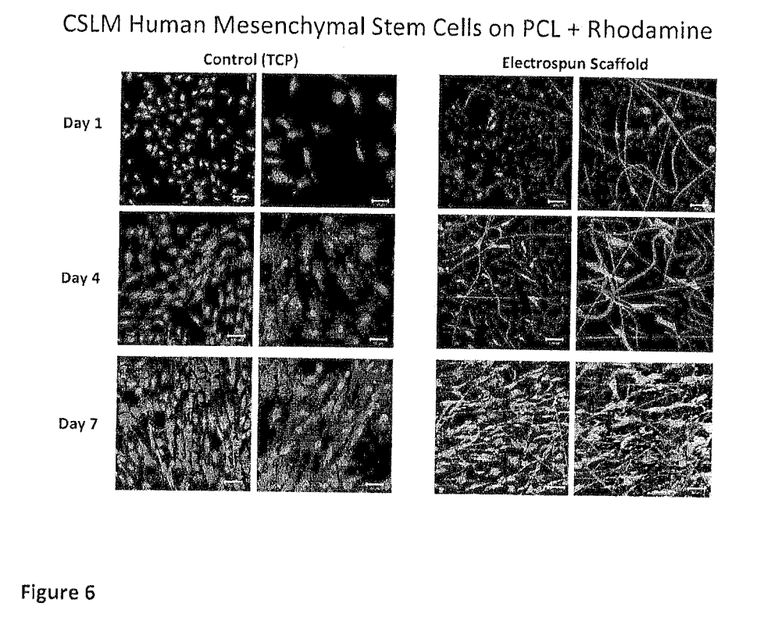
FIGS. 6 and 7 illustrate growth of human primary mesenchymal stem cells on an electrospun PCL scaffold.
Figure 7:
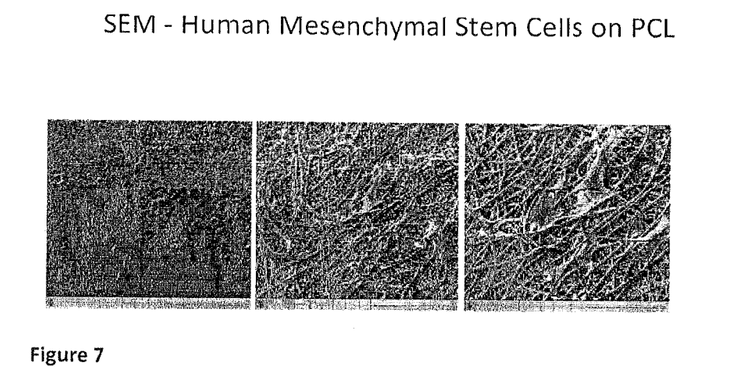

FIGS. 6 and 7 are similar to FIGS. 4 and 5, instead illustrating the growth of Human Primary Mesenchymal Stem Cells on the electrospun PCL scaffold. FIG. 6 shows the results of a comparative test in which the Human Primary Mesenchymal Stem Cells were cultured on the electrospun PCL scaffold, and on control TCP. This was achieved using the same Normal Growth Medium used with the hDF cells i.e. DMEM (high glucose) supplemented with 10% fetal bovine serum and 1% penicillin/streptomycin. The dye Rhodamine B was used to improve visibility of the electrospun PCL scaffold. The photomicrographs of FIG. 6 were taken using a Confocal Laser Scanning Microscopy (CSLM) technique. For each of the control and electrospun scaffold, the images shown include images of two levels of resolution taken on day 1 of the test, and also on day 4 and day 7.

FIG. 7 includes images of the Human Primary Mesenchymal Stem Cells on the PCL scaffold on day 3 of the test, taken instead using a Scanning Electron Microscopy (SEM) technique, and with three levels of increasing magnification for each day. This illustrates the cell growth which took place on the electrospun polymer scaffold.

Figure 8:
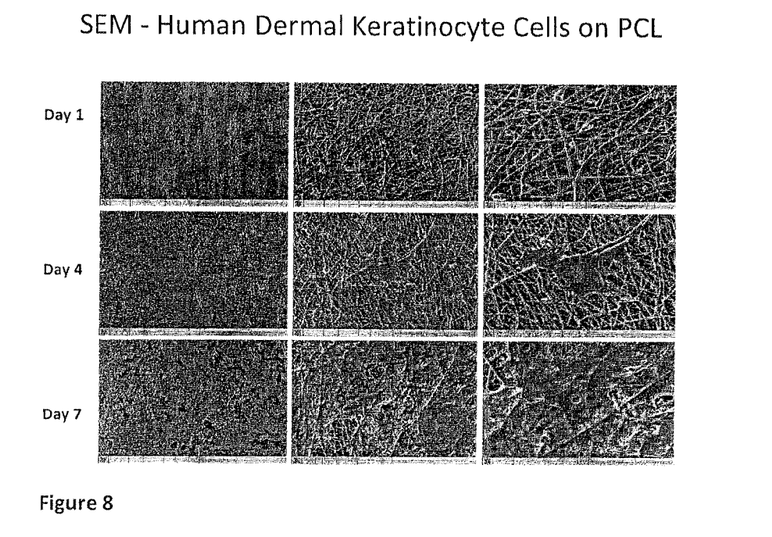
FIG. 8 illustrates growth of human dermal keratinocyte (hDK) cells on an electrospun PCL scaffold.

FIG. 8 is similar to FIG. 5, this time illustrating the growth of Human Dermal Keratinocyte Cells on the electrospun PCL scaffold, which were cultured in a suitable growth medium for this cell type. In this case, the growth medium was DMEM (high glucose) supplemented with 2 mM L-glutamine, 10% fetal calf serum and 1% Penicillin/Streptomycin. FIG. 8 includes images of the scaffold at three levels of magnification on each of days 1, 4 and 7 of the test, illustrating the growth of the cells. These images were taken using an SEM technique. No control images are present in this case.

Figure 9:
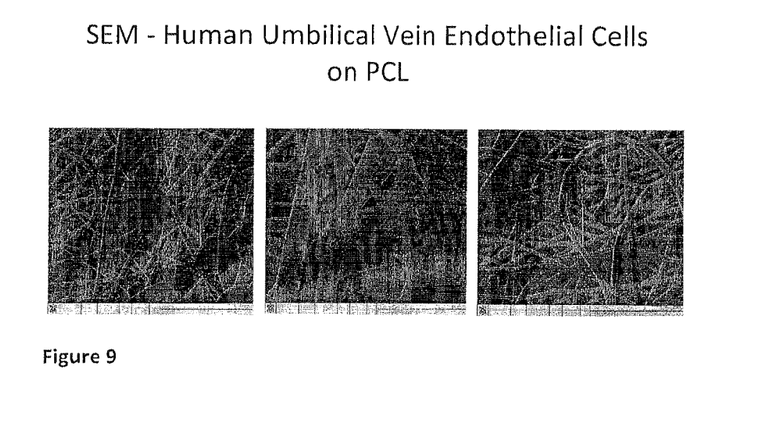
FIG. 9 shows growth of human primary umbilical vein endothelial (hUVE) cells on an electrospun PCL scaffold.

FIG. 9 is similar to FIG. 7, but this time illustrating the growth of Human Primary Umbilical Vein Endothelial Cells on the electrospun PCL scaffold when cultured using a suitable growth medium. In this case, the growth medium was DMEM (high glucose) supplemented with 10% fetal bovine serum, 1% penicillin/streptomycin and endothelial cell growth supplement (commercially available from Sigma-Aldrich, UK).

FIG. 9 includes images of the scaffold at three levels of magnification on day 1 (after 24 hours) illustrating the growth of the cells. These images were taken using an SEM technique. No control images are present in this case.

This testing provided evidence that electrospun scaffolds supported the culture of the cell types employed in the study which have strong application in the area of cardiovascular and dermal tissue engineering.

Effect of Plasma Treatment

Some further examples were carried out to investigate the role of plasma in electrospun tissue scaffold production.

In each of these examples, a control test scaffold was produced using electrospun PCL under the conditions described above in relation to FIG. 3. Thus the composition used was 10% weight by volume PURASORB® PLC 7015 70/30 L-lactide/caprolactone copolymer, IV midpoint 1.5 dl/g in a solvent comprising 90% chloroform and 10% dimethylformamide (DMF). A voltage of 10 kV was applied to the spinneret, and the polymer flow rate was 1 ml/hour. The ambient temperature within the apparatus housing was approximately 23 degrees Celsius. The needle gauge was 18 G. An extractor fan coupled to the housing was set at a high level to rapidly remove the evaporating fumes from the solvents. This scaffold was not plasma treated, and is referred to as the "untreated scaffold".

Another scaffold was produced in accordance with the invention under the same spinning conditions outlined in relation to obtaining the PCL electrospun scaffold FIG. 3 above, but this time using the plasma treatment apparatus to treat the electrospun PURASORB® PLC 7015 70/30 L-lactide/caprolactone copolymer, IV midpoint 1.5 dl/g fibers, in the region between the spinneret and test scaffold template. Thus once more the composition used was 10% weight by volume of the PURASORB® PLC 7015 in a solvent comprising 90% chloroform and 10% dimethylformamide (DMF). A voltage of 10 kV was applied to the spinneret, and the polymer flow rate was 1 ml/hour. The ambient temperature within the apparatus housing was approximately 23 degrees Celsius. The needle gauge was 18 G. An extractor fan coupled to the housing was set at a high level to rapidly remove the evaporating fumes from the solvents. The plasma utilised in this instance was a dielectric barrier discharge (DBD) atmospheric gas plasma. The plasma treatment was carried out at a power of 750 W over 5 cycles and under the ambient atmospheric conditions. This scaffold is referred to as the "plasma treated" scaffold.

Neither of the plasma treated or untreated scaffolds were subjected to heat treatment after formation in this test and prior to being populated with cells. The untreated and treated scaffolds were produced under identical conditions other than that one scaffold was plasma treated, and the other was not. The template was not rotated during the electrospinning process for either the control or plasma treated scaffolds.

Figure 10:
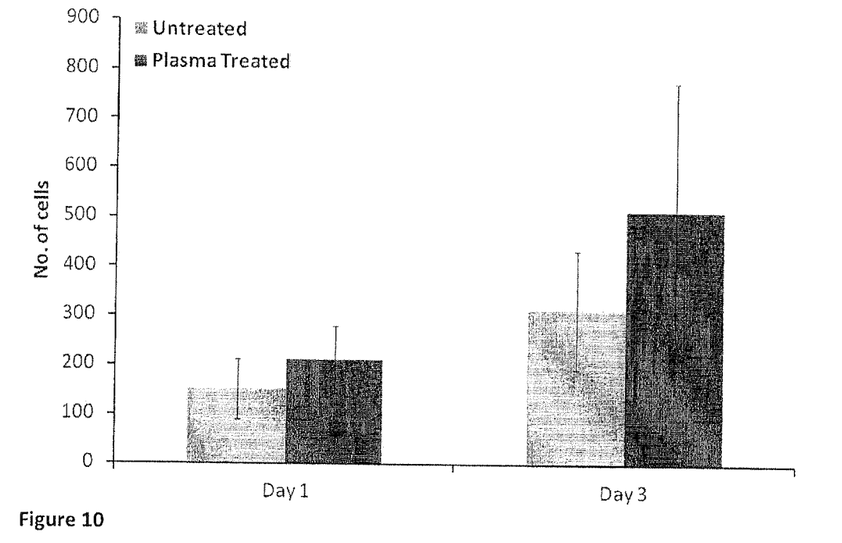
FIG. 10 shows the effect of the plasma treatment on hDF cell growth.

FIG. 10 illustrates the results when each of the untreated (the lighter bars on the left for each day) and plasma treated (the darker bars on the right for each day) electrospun PCL scaffolds were populated with Human Primary Dermal Fibroblast (hDF) cells in a "Normal growth medium", being the DMEM (high glucose) supplemented with 10% fetal bovine serum and 1% penicillin/streptomycin.

FIG. 10 records the number of cells counted on each of the scaffolds on day 1 and day 3 measured from the start of the cell culture process. It may be seen that the number of cells found to be present on the treated scaffold was higher than that found upon the untreated scaffold. The difference was found to be statistically significant, such that the p-value was <0.05 on day 3.

Figure 11:
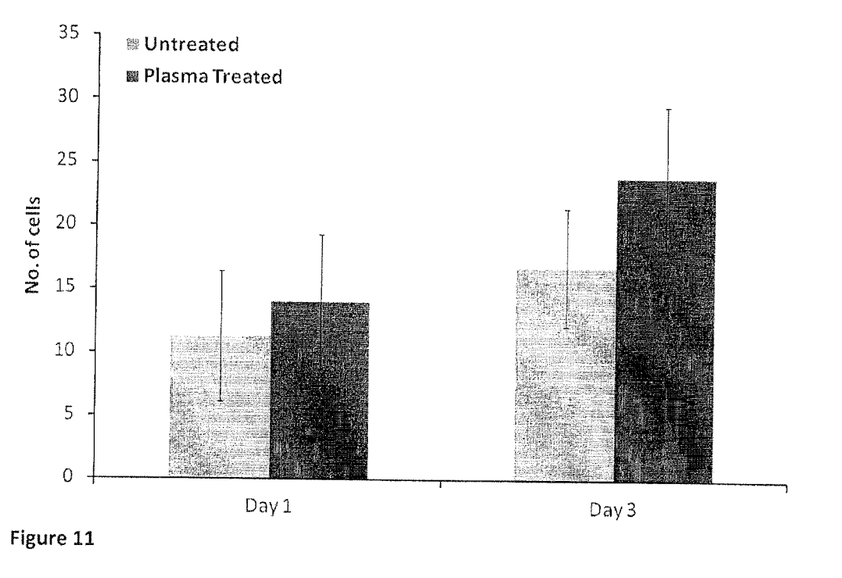
FIG. 11 shoes the effect of the plasma treatment on human primary coronary artery smooth muscle (hCASM) cell growth.

FIG. 11 illustrates the results when each of an untreated (the lighter bars on the left for each day) and plasma treated (the darker bars on the right for each day) electrospun PCL scaffold was populated with Human Primary Coronary Artery Smooth Muscle (hCASM) cells in a suitable growth medium. In this case, the growth medium was the same "Normal growth medium" as used for the hDF cells described in relation to FIG. 10. FIG. 11 records the number of cells counted on each of the scaffolds on day 1 and day 3 measured from the start of the cell culture process. It may be seen that the number of cells found to be present on the treated scaffold was higher than that found upon the untreated scaffold. The difference was found to be statistically significant, such that the p-value was <0.05 on day 3.

The cell counts in reported in FIGS. 10 and 11 were obtained by using a nuclear cell counting application whereby it is assumed that one nucleus is present in every cell. The cells were labelled with 7AAD which binds to the nucleic acid present in the cells. Images of the cells were then taken using a fluorescent microscope and the number of cells per field of view calculated. Between 20 and 30 fields of view per sample were taken. These images were analysed using the Volocity® Image analysis software by Perkin-Elmer®. It was therefore found that the plasma treatment of scaffolds produced preferential cell numbers after 3 days in culture as illustrated by the cell counts performed for the HDF and HCASM cells tested.

The invention claimed is:

1. A method of forming a tissue scaffold, the method comprising:
   providing an electrospinning apparatus comprising a spinneret, a tissue scaffold template spaced from the spinneret, an anode and a cathode spaced apart from the anode, the anode and the cathode positioned between the spinneret and the template;
   applying a voltage to each of the anode and the cathode to generate a region of plasma therebetween; and
   electrospinning a polymer from the spinneret onto the template, by electrospinning the polymer through the region of plasma to expose the polymer to a plasma, to form the tissue scaffold.

2. The method of claim 1, further comprising the steps of:
   electrospinning a first polymer layer onto the template; and
   electrospinning a second polymer layer onto the template;
   wherein the template rotates during the electrospinning of one of the first and second polymer layers, and wherein the template does not rotate during the electrospinning of the other of the first and second polymer layers.

3. The method of claim 2, wherein only one of the first and second polymer layers is exposed to said plasma.

4. The method of claim 2, wherein both the first and the second polymer layers are exposed to said plasma.

5. The method of claim 2, wherein the first and second polymer layers comprise the same polymer.

6. The method of claim 2, wherein the first and second polymer layers comprise different polymers.

* * * * *